(12) United States Patent
Graham

(10) Patent No.: US 6,558,339 B1
(45) Date of Patent: May 6, 2003

(54) FOOT ALLEVIATOR

(76) Inventor: Michael E. Graham, 39 Fourth St., Suite 204, Laurel, MD (US) 20707

( * ) Notice: Subject to any disclaimer, the term of this patent is extended or adjusted under 35 U.S.C. 154(b) by 0 days.

(21) Appl. No.: 09/443,326

(22) Filed: Nov. 19, 1999

(51) Int. Cl.[7] .............................. A61F 5/00; A61F 13/00
(52) U.S. Cl. ......................... 602/66; 602/23; 128/882
(58) Field of Search .......................... 602/5–6, 23, 27, 602/60–62, 65–66, 75; 128/882, 889, 892–894; 36/145, 154, 166, 173, 174

(56) References Cited

U.S. PATENT DOCUMENTS

| | | |
|---|---|---|
| 892,652 A | 7/1908 | Dahlmann |
| 1,025,571 A | 5/1912 | Howe |
| 1,406,583 A | 2/1922 | Ruge |
| 1,492,514 A | 4/1924 | Jensen |
| 1,614,934 A | 1/1927 | Saums |
| 1,741,340 A | 12/1929 | Scholl |
| 1,788,852 A | 1/1931 | Arthur |
| 1,837,488 A | 12/1931 | Romero |
| 1,952,538 A | 3/1934 | Devine |
| 2,255,100 A * | 9/1941 | Brady ............................ 36/71 |
| 2,790,975 A * | 5/1957 | McCormick ................... 2/239 |
| 4,001,955 A * | 1/1977 | Turner, Jr. ..................... 36/96 |
| 4,085,745 A | 4/1978 | Alenares |
| 4,314,412 A * | 2/1982 | Anderson et al. ............. 36/100 |
| 4,351,324 A | 9/1982 | Bronkhorst |
| 4,476,858 A * | 10/1984 | Curtis ......................... 128/80 |
| 4,510,699 A | 4/1985 | Nakamura et al. ............. 36/43 |
| 4,841,957 A | 6/1989 | Wooten |
| 4,862,604 A | 9/1989 | Hauser |
| 4,969,277 A * | 11/1990 | Williams ....................... 36/97 |
| 5,092,347 A * | 3/1992 | Shaffer et al. ............. 128/892 |
| 5,176,624 A * | 1/1993 | Kuehnreich ................... 602/65 |
| 5,310,400 A * | 5/1994 | Rogers et al. .................. 602/5 |
| 5,460,601 A | 10/1995 | Shannahan |
| 5,554,107 A | 9/1996 | Shannahan |
| 5,611,153 A | 3/1997 | Fisher |
| 5,617,745 A | 4/1997 | Della Corte |
| 5,645,525 A | 7/1997 | Krivosha |
| 5,713,143 A * | 2/1998 | Kendall ....................... 36/145 |
| 5,718,673 A | 2/1998 | Shipstead |
| 5,776,090 A | 7/1998 | Bergman |
| 5,833,640 A | 11/1998 | Vazquez, Jr. |
| 5,840,053 A | 11/1998 | Roth |
| 5,865,779 A | 2/1999 | Gleason |
| 5,887,591 A | 3/1999 | Powell |
| 5,891,073 A * | 4/1999 | Deirmendjian et al. ....... 602/27 |
| 5,944,679 A | 8/1999 | DeToro |
| 6,026,599 A * | 2/2000 | Blackwell et al. ............ 36/140 |
| 6,154,983 A * | 12/2000 | Austin ........................... 36/12 |

\* cited by examiner

*Primary Examiner*—Denise M. Pothier
(74) *Attorney, Agent, or Firm*—Kile Goekjian Lerner & Reed; Bradford E. Kile

(57) ABSTRACT

The present invention is a removable semi-elastic brace which may alleviate heel and arch pain. The present invention provides support to the heel and arch of the foot to aid in the treatment of plantar fasciitis, heel spur syndrome, calcaneal apophysitis, and Achilles tendinitis and tibialis posterior dysfunction. The device is adjustable to accommodate small changes in foot size. The device may also be used in conjunction with other treatment modalities including night or rest splints and custom-molded orthotics.

7 Claims, 6 Drawing Sheets

FOOT ALLEVIATOR

FIELD OF THE INVENTION

The present invention aids in the treatment of plantar fasciitis. More particularly to a foot brace that aids in the treatment of plantar fasciitis.

BACKGROUND OF THE INVENTION

There is a growing number of the population developing a severe inflammation of a long thick ligament on the bottom of the foot. This ligament, plantar fascia, has three bands, inner, central and outer. The inner and central bands are the thickest and most used portion of the ligament.

The plantar fascia originates on the plantar, bottom, of the calcaneus, heel bone, and inserts in the area of the ball of the foot. The function of the plantar fascia is to maintain an arch in the foot. Usually, injury occurs to this ligament due to the foot type, either a high or low arch, tight Achilles tendon, poor shoe gear, obesity, and overuse such as prolonged standing or walking over a long period of time.

The continued over-stretching of the plantar fascia produces micro-ruptures on the inner and central bands of the ligament.

An outgrowth of bone on the bottom of the heel where the ligament attaches is due to the chronic pulling of the ligament on the bone; the "heel spur" actually helps the situation by decreasing the pull of the ligament.

Various treatments exist for plantar fasciitis. Non-surgical, conservative, forms of treatment of this condition are quite successful when used in combination. Currently, the various modalities used in treatment of this condition include: steroid injections, oral medications (anti-inflammatory), taping and strapping of the foot, physical therapy, arch supports which are custom-molded and also over-the-counter arch supports, heel cups, splints to be worn at night or while resting, elastic foot supports, change in physical activities, change in diet and weight loss, change in shoe gear, change in occupation and also work habits, application of hard or soft casts, or a prolonged period of non-weightbearing with crutches.

Steroid injections are potentially dangerous. The effects of steroid injections can weaken the ligament, therefore only three to four injections are given over a prolonged period. Some patients will not consent to an injection.

Anti-inflammatory medications are of help if they can be prescribed. Contra-indications include allergic reaction to the medication and stomach ulcers; these patients cannot take this medication. Even with the specially coated medication patients still complain of stomach irritation. There are also issues of cost and patient compliance.

Applying tape to the foot is helpful in decreasing the pull of the ligament. A doctor or other qualified medical professional usually performs this procedure. Problems occur when patients are allergic to the adhesive tape. They develop very painful blisters that can take weeks before they are resolved. Another problem is bathing; plastic bags and other methods have to be used in order to perform these duties. Other applied devices such as soft or hard casts will have the same problem and are very impracticable.

Physical therapy is primarily used in addressing only the inflammatory aspect of the injury. Usually, the patient must attend at least three to four sessions a week for several weeks. There are no preventative measures taken to decrease the pull on the plantar fascia.

There are several patents used for holding the foot in a stable position while at rest, either night or rest splints. These devices are very bulky, limit the wearer to minimal weightbearing, can only be worn during periods of rest, one cannot wear shoes with these devices, and they are very expensive.

Custom-molded arch supports, orthotics, or over-the-counter arch supports are only effective when the patient is wearing their shoes. Orthotics and over the counter arch supports can be very expensive, do not fit in all shoe styles, and are not helpful when the patient is not wearing shoes.

Other forms of elastic wraps do not address the most important aspect of the heel pain. Measurements are not taken to take pressure off of the most painful part of the heel while walking. Elastic wraps only try to decrease pressure on the pull of the plantar fascia. Additionally, elastic wraps are constructed of a constricting material that does not allow for moisture evaporation.

A heel cup may also be used to compress the anatomical fat pad to the bottom of the heel. Heel cups may actually add pressure to the painful part of the heel and may lead to further discomfort. Also, a heel cup may only be worn in a shoe.

These disadvantages, are solved by the present invention.

SUMMARY OF THE INVENTION

The present invention provides a brace which is a semi-elastic bandage and may alleviate pain attributed to the plantar fascia. The brace provides support and may be removed for bathing and reapplied. The brace also has an elastic nature to control the amount of compression in an effort to relieve the stress on the plantar fascia. A special heel modification is incorporated in the brace in order to bear the weight of the user while also disallowing pressure to be applied to the painful part of the heel.

The brace is generally off-weighting the painful aspect of the heel while weightbearing, and to support the arch of the foot to prevent stretching of the plantar fascia.

The brace may be easily removed and reapplied by the user without the assistance of a medically qualified professional. The brace may also be worn with or without shoes and in conjunction with other arch supports.

The brace also contains a medial arch pad that decreases the pull on the plantar fascia therefore reducing the pull on the injured portion of the ligament. This facilitates ligament healing and prevents further irritation and damage to the ligament.

A semi-elastic material has fenestrations that allow for moisture evaporation, and also accommodate small changes in foot size. Since there is no elastic or adhesives in contact with the skin there are currently no contra-indications for patients with allergies to these materials.

The brace may also be worn with other external rest or night splints, and may be made in different sizes to allow the brace to be more custom fit. The elasticity allows the user to be mobile while other devices immobilize. The brace may be worn with or without shoes and in conjunction with other arch supports.

A semi-compressible heel pad located within the brace is specifically designed to allow for weightbearing without applying pressure to the painful portion of the heel. The heel is taken into consideration.

The present invention brace, an effective aid in the treatment of heel and arch pain (plantar fasciitis), may also be used in the treatment of Achilles tendinitis, Sever's disease (calcaneal apophysitis), and Haglund's syndrome and tibialis anterior dysfunction.

BRIEF DESCRIPTIONS OF THE DRAWINGS

DETAILED DESCRIPTION OF THE INVENTION

Figure 1:
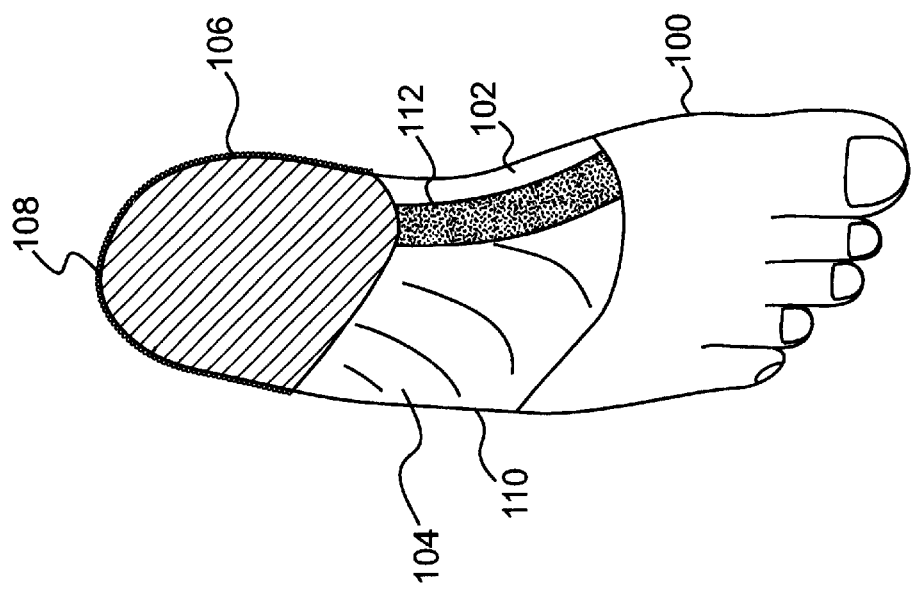
FIG. 1 is a top view of the present invention shown on a foot.

Referring now to the figures, FIG. 1 illustrates a top view of the present invention foot brace 110 on users foot 100. Foot brace 110 has upper left portion 104 and upper right portion 102 which are secured on the top of users foot 100.

Upper left portion 104 and upper right portion 102 are preferably secured by velcro 112. Foot brace 110 also has left back heel portion 108 and right back heel portion 106 which are secured together.

Figure 2:
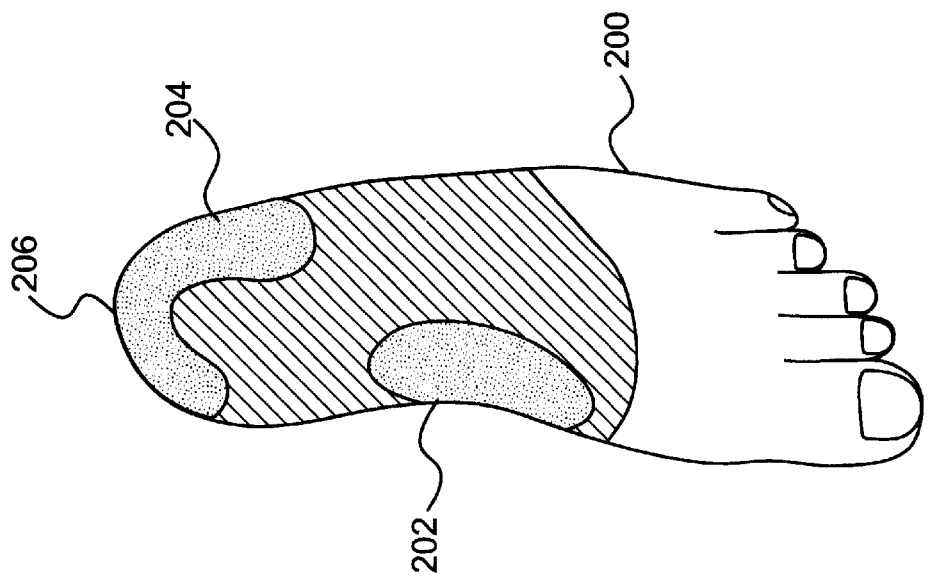
FIG. 2 is a bottom view of the present invention shown on a foot.

FIG. 2 illustrates foot brace 206 on users foot 200. Foot brace 206 has medial arch pad 202 and heel pad 204.

Figure 3:
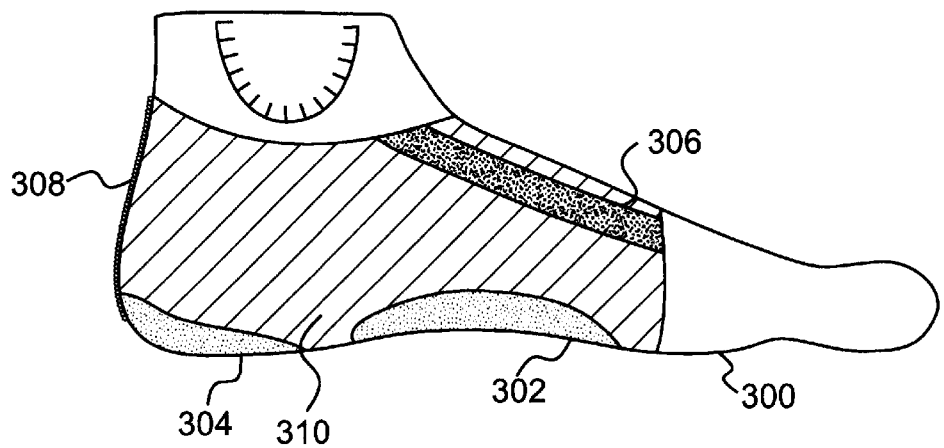
FIG. 3 is a side view of the present invention shown on a foot.

FIG. 3 illustrates foot brace 310 on users foot 300. Foot brace 310 has medial arch pad 302 and heel pad 304 attached. Velcro 306 secures foot brace 310 to users foot 300. Velcro 308 attaches left heel portion and right heel portion thereby securing foot brace 310 to users foot 300.

Figure 4:
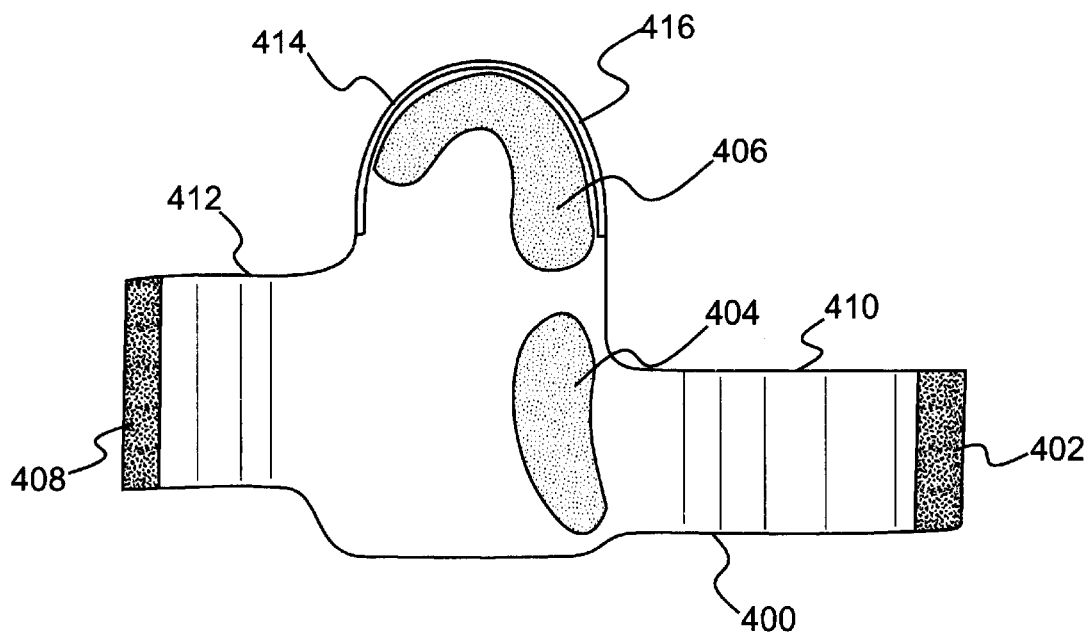
FIG. 4 is a top view of the present invention.

FIG. 4 illustrates the preferred embodiment of foot brace 400 having medial arch pad 404 and heel pad 406. Upper right portion 410 of foot brace 400 is secured to upper left portion 412 of foot brace 400 by velcro 402 and velcro 408. Foot brace 400 has left back heel portion 414 and right back heel portion 416. Left back heel portion 414 and right back heel portion 416 are preferably sewn together to form a cup which surrounds the heel of the foot.

Figure 5:
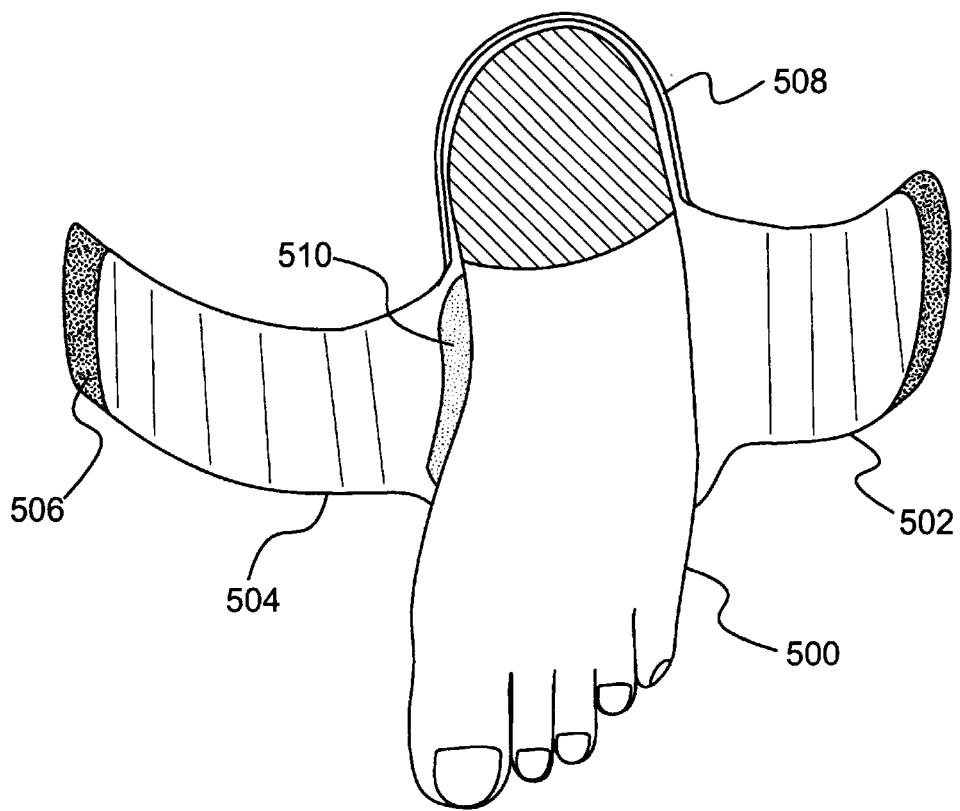
FIG. 5 is a top view of the present invention shown on a foot.

FIG. 5 illustrates foot brace 508 before it is secured to users foot 500. Foot brace 508 has upper right portion 502 and upper left portion 504. Upper left portion 504 has velcro 506. Medial arch pad 510 is shown attached to foot brace 508.

Figure 6:
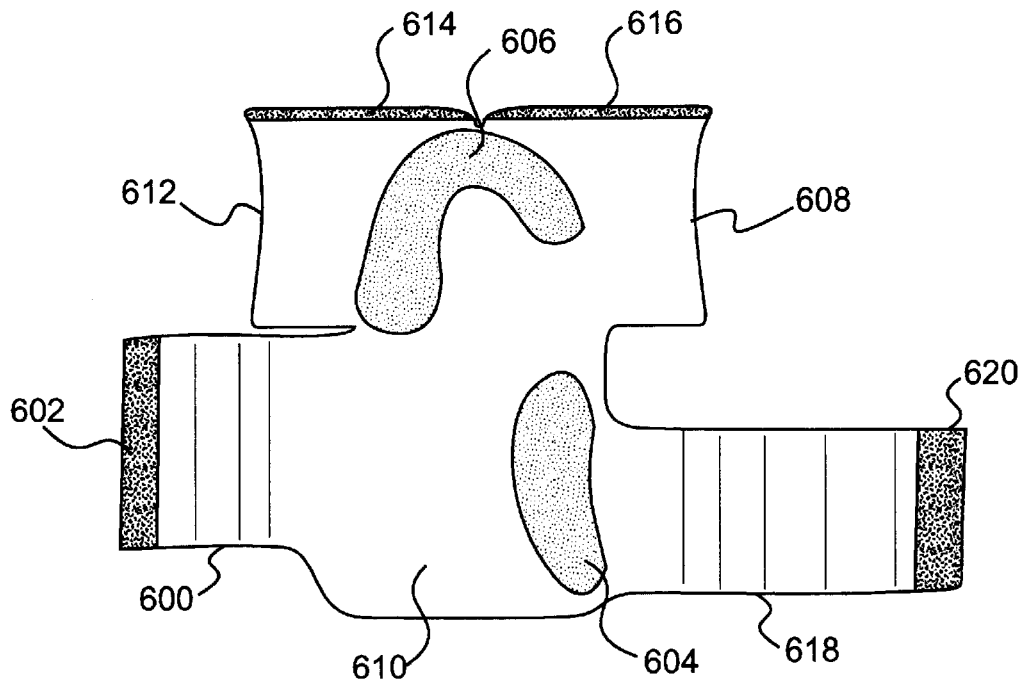
FIG. 6 is a top view of the present invention.

FIG. 6 illustrates foot brace 610. Foot brace 610 contains medial arch pad 604 and heel pad 606. Foot brace 610 also has upper left portion 600 containing velcro 602. Foot brace 610 also has upper right portion 618 having velcro 620. Velcro 602 of upper left portion attaches to velcro 620 of upper right portion 618 to secure foot brace 610 to the users foot.

Foot brace 610 has left back heel portion 612 having velcro 614. Foot brace 610 also has right back heel portion 608 having velcro 616. Velcro 614 also secures foot brace 610 to the users foot by attaching to velcro 616. While sewing right back heel 608 portion and left back heel portion 612 is preferred, FIG. 6 illustrates the use of velcro to attach right back heel portion 608 to left back heel portion 612.

Figure 7:
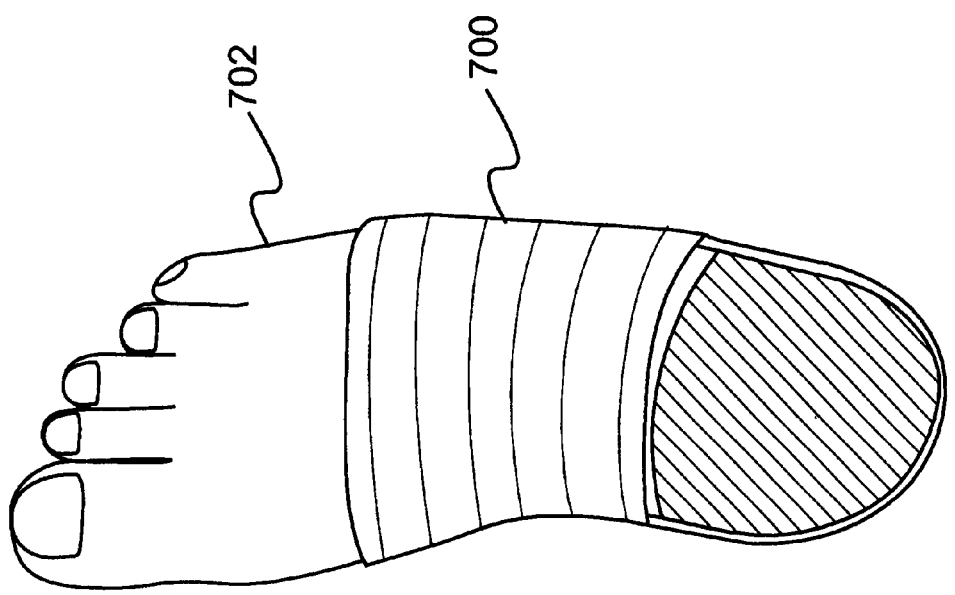
FIG. 7 is a top view of the present invention shown on a foot.

FIG. 7 illustrates foot brace 700 wrapped around the top of users foot 702.

Figure 8:
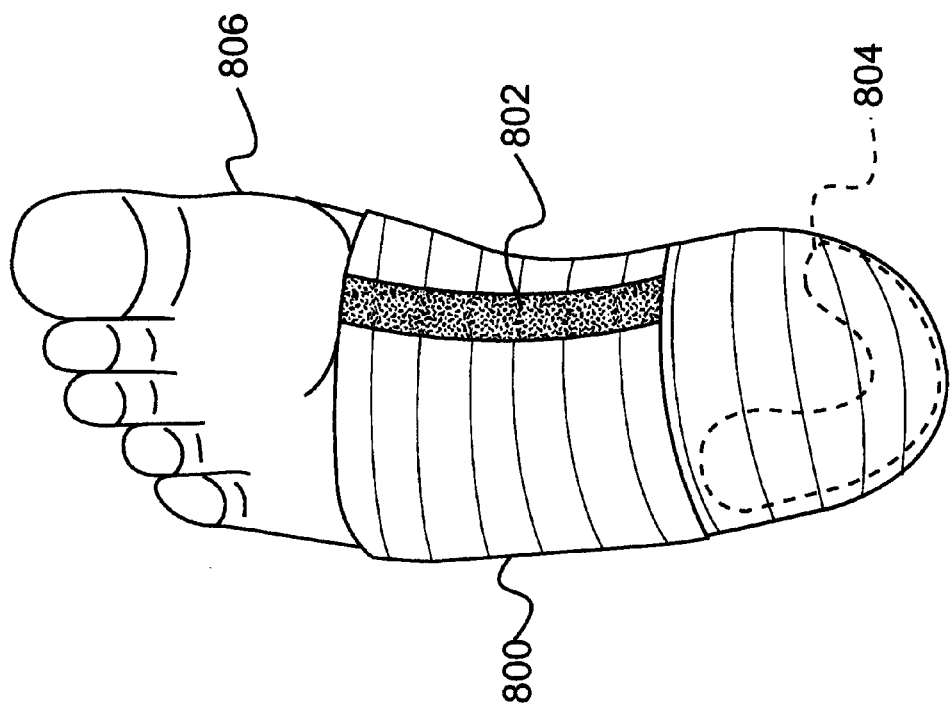
FIG. 8 is a bottom view of the present invention shown on a foot.

FIG. 8 illustrates foot brace 800 as shown from the bottom of users foot 806. Foot brace 800 is shown with heel pad 804 and velcro 802 securing foot brace 800 to users foot 806.

Figure 9:
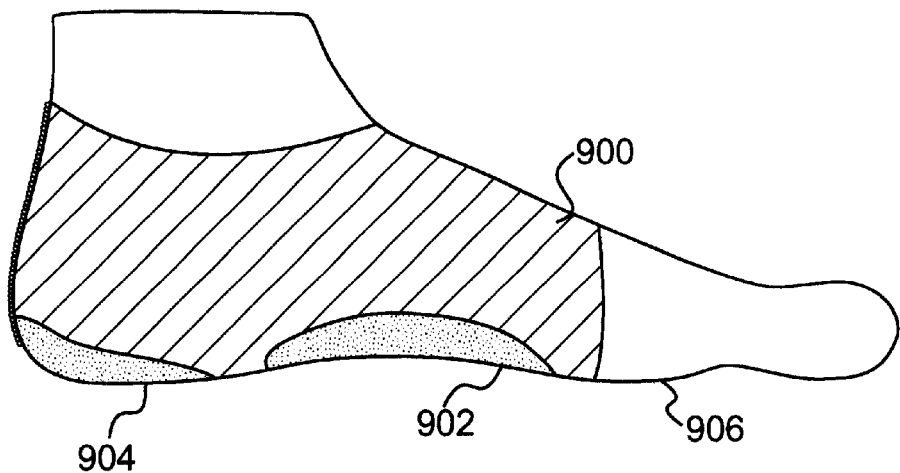
FIG. 9 is a side view of the present invention shown on a foot.

FIG. 9 illustrates foot brace 900 having heel pad 904 and medial arch pad 902. Foot brace 900 is shown secured to users foot 906.

Figure 10:
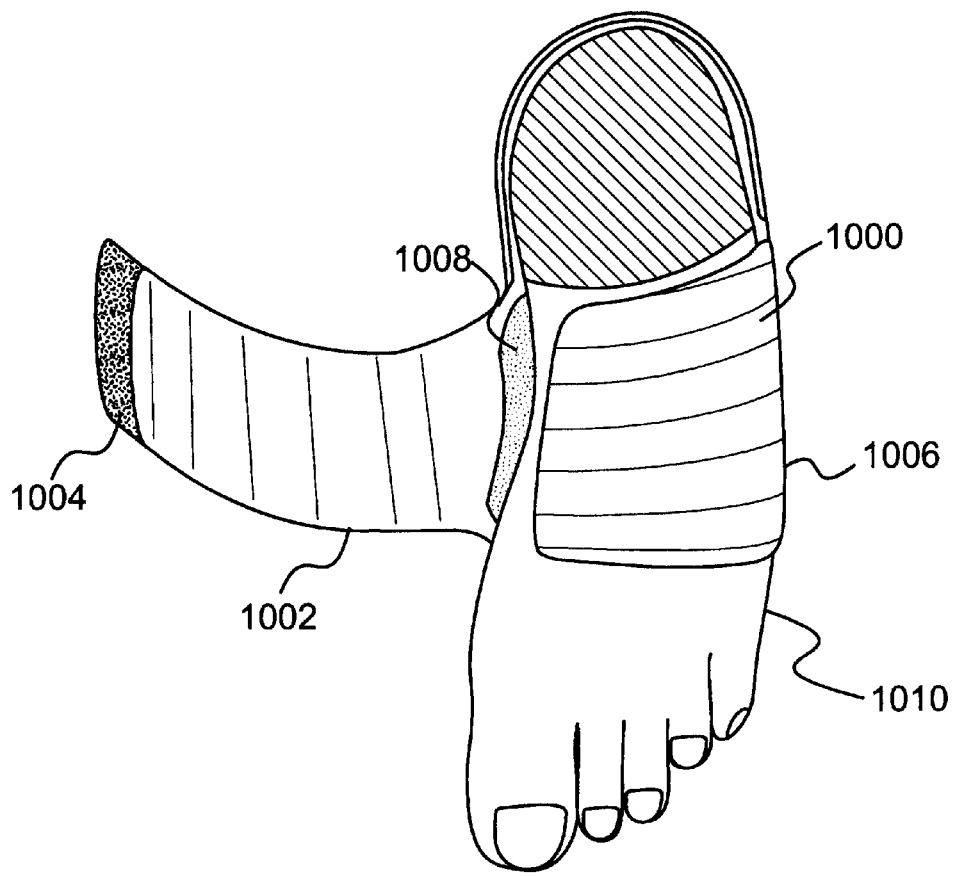
FIG. 10 is a top view of the present invention shown on a foot.

FIG. 10 illustrates foot brace 1000 having upper right portion 1006 and upper left portion 1002 having velcro 1004. Foot brace 1000 has medial arch pad 1008. Foot brace 1000 is shown on users foot 1010.

Figure 11:
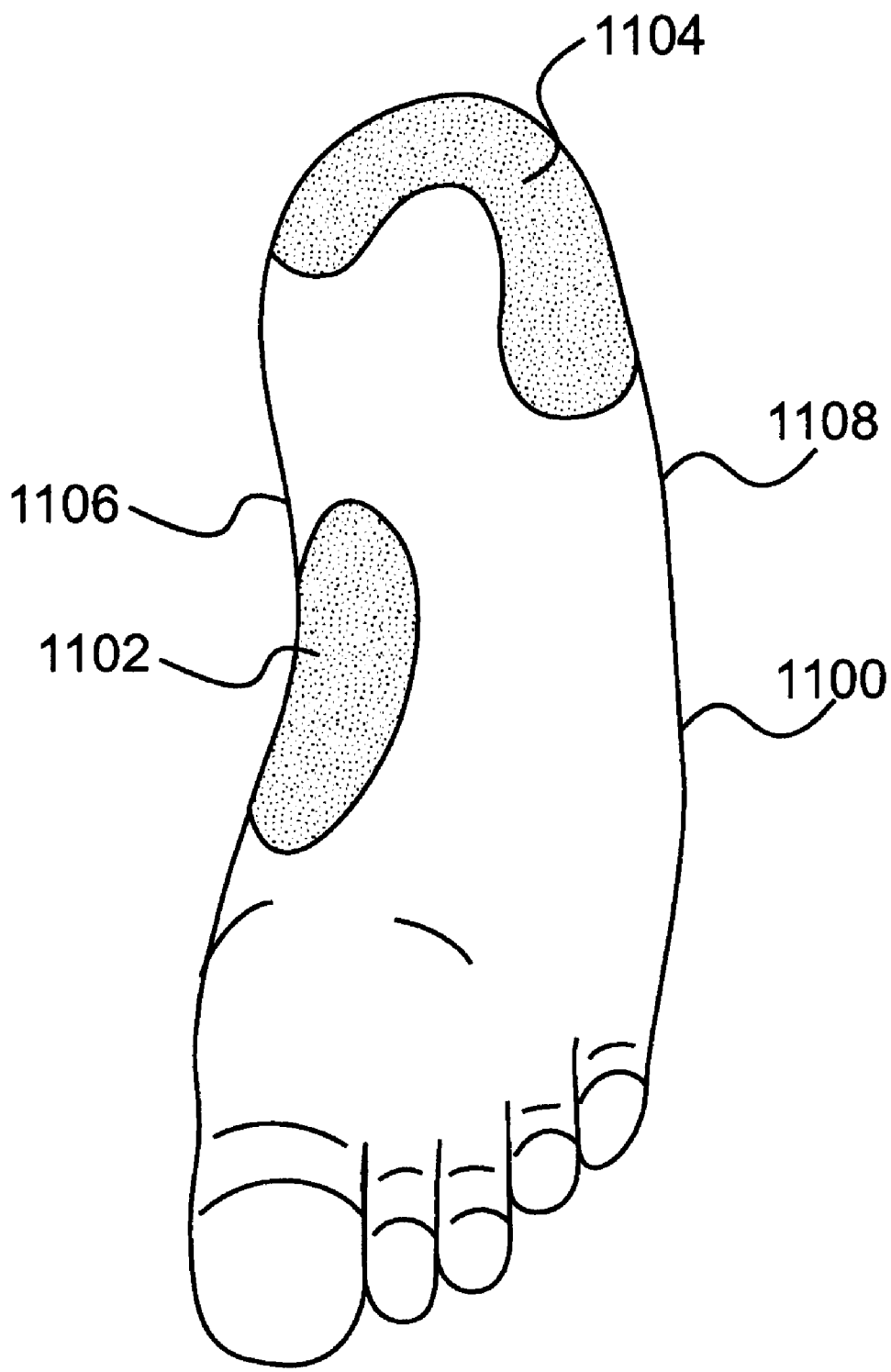
FIG. 11 is a bottom view of pieces of the present invention shown on a foot.

FIG. 11 illustrates medial arch pad 1102 and the preferred embodiment for heel pad 1104, shown on the bottom of users foot 1100. The preferred shape of heel pad 1104 is such that the portion of heel pad 1104 that is located under inner side 1106 of users foot 1100 is shorter than the portion of heel pad 1104 that is located under outer side 1108 of users foot 1100.

While the preferred embodiment and various alternative embodiments of the invention have been disclosed and described in detail herein, it may be apparent to those skilled in the art that various changes in form and detail may be made therein without departing from the spirit and scope thereof.

What is claimed is:

1. A foot device, comprising:
    a semi-elastic bandage comprising a medial arch pad and a heel pad, attached to said bandage, the medial arch pad being separate and spaced from the heel pad along the bandage,
    wherein said heel pad is shaped so that the portion of said heel pad that is located under the inner portion of the user's foot during use is shorter than the portion of said heel pad that is located under the outer portion of the user's foot during use,
    such that, when the user is standing upright, the user's weight does not bear on the user's heel bone at the point of insertion of the user's plantar fascia inner band into the user's heel bone, and
    wherein said bandage further comprises,
        an upper left portion and an upper right portion which rests upon the top of the user's foot during use; and
        a securing means for securing said upper left portion and said upper right portion together.

2. The device as defined in claim 1, wherein the securing means comprises:
    a hook and loop fastener attached to the upper left portion of said bandage;
    a hook and loop fastener attached to the upper right portion of said bandage, and
    wherein said hook and loop fastener attached to the upper left portion of said bandage attaches to said hook and loop fastener attached to the upper right portion of said bandage to secure the bandage to the user's foot.

3. The device as defined in claim 1, wherein said bandage further comprises:
    a back heel cup sized and configured to hold and surround the user's heel.

4. The device as defined in claim 1, wherein said bandage further comprises:
   a left back heel portion and a right back heel portion sized and configured to enclose the back of the users heel, and
   a securing means for securing said left back heel portion and said right back heel portion together.

5. The device as in claim 4, wherein the securing means comprises:
   a hook and loop fastener attached to the left back heel portion of said brace;
   a hook and loop fastener attached to the right back heel portion of said brace, and
   wherein said hook and loop fastener attached to the left back heel portion of said brace attaches to said hook and loop fastener attached to the right back heel portion of said brace to secure the brace to the users foot.

6. The device as in claim 4, wherein the securing means comprises thread to sew the left back heel portion of said bandage to the right back heel portion of said bandage.

7. The device as in claim 1, wherein said bandage is toeless.

* * * * *